(12) United States Patent
Hasui

(10) Patent No.: US 9,433,772 B2
(45) Date of Patent: Sep. 6, 2016

(54) ELECTRODE DEVICE USED IN IONTOPHORESIS TREATMENT

(75) Inventor: Akihiro Hasui, Higashikagawa (JP)

(73) Assignee: TEIKOKU SEIYAKU CO., LTD., Higashikagawa-Shi (JP)

( * ) Notice: Subject to any disclaimer, the term of this patent is extended or adjusted under 35 U.S.C. 154(b) by 1112 days.

(21) Appl. No.: 13/518,343

(22) PCT Filed: Dec. 17, 2010

(86) PCT No.: PCT/JP2010/072744
§ 371 (c)(1),
(2), (4) Date: Aug. 29, 2012

(87) PCT Pub. No.: WO2011/078071
PCT Pub. Date: Jun. 30, 2011

(65) Prior Publication Data
US 2012/0330217 A1 Dec. 27, 2012

(30) Foreign Application Priority Data

Dec. 22, 2009 (JP) ................................ 2009-290943

(51) Int. Cl.
*A61N 1/30* (2006.01)
*A61N 1/04* (2006.01)

(52) U.S. Cl.
CPC ........... *A61N 1/0448* (2013.01); *A61N 1/0432* (2013.01)

(58) Field of Classification Search
CPC .................... A61N 1/0448; A61N 1/0432
USPC ........................................................ 604/20
See application file for complete search history.

(56) References Cited

U.S. PATENT DOCUMENTS 4,383,529 A * 5/1983 Webster ................ A61N 1/044
604/20
4,752,285 A 6/1988 Petelenz et al.
(Continued)

FOREIGN PATENT DOCUMENTS

EP  0931684 A1  7/1999
EP  1177814 A1  2/2002
(Continued)

OTHER PUBLICATIONS

European Search Report issued in corresponding European Application EP10829301.

*Primary Examiner* — Theodore Stigell
(74) *Attorney, Agent, or Firm* — Birch, Stewart, Kolasch & Birch, LLP

(57) ABSTRACT

The present invention provides an electrode device used in iontophoresis treatment, in which an electrode layer used for introduction of medication can be contacted to a medication reservoir layer with a simple manner, and in which the medication reservoir layer can be reliably held when the medication is introduced into a skin. A main-electrode layer 3 and a sub-electrode layer 1 are secured on a substrate 6 while both the layers are being insulated from each other. The main-electrode layer 3 is intended for introduction of the medication, and the sub-electrode layer 1 is provided to hold the medication reservoir layer 5 on the substrate 6. The medication reservoir layer 5 is located on the substrate 6, so as to be in contact with the main-electrode layer 3 and the sub-electrode layer 1. The medication reservoir layer 5 is a gel containing halogen compound, and the sub-electrode layer 1 comprises a metal having a lower ionization tendency than hydrogen. The medication reservoir layer 5 and the sub-electrode layer 1 are bonded to each other by applying an electric current to both layers. In this way, the medication reservoir layer 5 can be firmly held on the substrate 6, while being kept in contact with the main-electrode layer 3.

6 Claims, 4 Drawing Sheets

(56) References Cited

U.S. PATENT DOCUMENTS

| | | | |
|---|---|---|---|
| 5,320,597 A * | 6/1994 | Sage, Jr. | A61N 1/303 604/20 |
| 5,766,144 A | 6/1998 | Lai et al. | |
| 6,185,453 B1 | 2/2001 | Hussain et al. | |
| 6,330,471 B1 | 12/2001 | Higo et al. | |
| 6,597,947 B1 | 7/2003 | Inoue et al. | |
| 6,915,159 B1 | 7/2005 | Kuribayashi et al. | |
| 2002/0161324 A1 | 10/2002 | Henley et al. | |
| 2003/0018295 A1 | 1/2003 | Henley et al. | |
| 2005/0113738 A1 | 5/2005 | Fuchita et al. | |
| 2005/0148996 A1 | 7/2005 | Sun et al. | |

FOREIGN PATENT DOCUMENTS

| | | |
|---|---|---|
| JP | 6059318 A | 3/1994 |
| JP | 8155041 A | 6/1996 |
| JP | 9248344 A | 9/1997 |
| JP | 2000-316991 A | 11/2000 |
| WO | WO-00/61220 A1 | 10/2000 |
| WO | WO-02/002182 A2 | 1/2002 |
| WO | WO-03/059442 A1 | 7/2003 |

* cited by examiner

ELECTRODE DEVICE USED IN IONTOPHORESIS TREATMENT

This application is the National Stage under 35 U.S.C. §371 of International Application No. PCT/JP2010/072744 filed on Dec. 17, 2010, which claims priority under 35 U.S.C. §119(a)-(d) of Patent Application No. 2009-290943 filed in Japan on Dec. 22, 2009.

TECHNICAL FIELD

The present invention relates to an electrode device, which is used in iontophoresis treatment wherein a voltage is applied to an electrically charged medication to thereby introduce the medication into a human body. In particular, the present invention relates to an electrode structure for the electrode device, by which an electrode layer and a medication reservoir layer in the electrode device can completely contact with each other, and thereby the medication reservoir layer can be reliably held when the medication is introduced.

BACKGROUND ART

Generally, in the iontophoresis treatment, a liquid or a gel containing the medication is made contact with a human skin (skin and mucosa), and an electric current is applied there, such that the medication ionically migrate into the skin, or into the body through the skin. An electrode device used in this treatment comprises an electrode layer and a medication reservoir layer, wherein the electrode layer is electrically charged from an external electric supply. The medication reservoir layer retains the ionized medication, thus having electric conductivity, and functions as an electrode device together with the electrode layer.

The medication reservoir layer can be in the form of a liquid or a gel. The medication reservoir layer is made contact with the electrode layer to function as a part of the electrode device, while introducing the medication retained therein into the skin. Therefore, the medication reservoir layer is needed to be firmly secured to the electrode device. Thus, there hitherto have been made various attempts to prevent the medication reservoir layer from leaking, peeling or dropping from the electrode device.

Patent Publication 1 discloses the use of a sheet substrate having a recess filled with a liquid or a gel (a medication reservoir layer). However, since the substrate having the recess is often turned upside down in practical use, the gel filling the recess is likely to flow down or drop off the recess.

Patent Publication 2 proposes an idea, wherein a non-woven fabric of a porous material is laminated on an electrode layer, and this non-woven fabric is impregnated with gel to thereby prevent the gel from dropping off. This publication also proposes an idea to mount a guide after the non-woven fabric is impregnated with the gel, the guide is for preventing the gel from dropping off.

Patent Publication 3 proposes a method, wherein a circular cup-shaped chamber is filled with a medication reservoir layer, and the chamber is closed with an ion permeable film. In Patent Publication 4, viscous gel is used to enhance the adhesive strength between an electrode layer and a medication reservoir layer.

PRIOR ART LITERATURE

Patent Publications

Patent Publication 1: JP-A-2000-316991
Patent Publication 2: WO2003/059442
Patent Publication 3: JP-A-H9-248344
Patent Publication 4: WO2002/002182 (JP-A-2004-501727)

SUMMARY OF THE INVENTION

Problem to be Solved by the Invention

It can be understood that any of the prior art inventions has been completed, as a result of the intensive efforts for bonding the medication reservoir layer to the electrode layer. However, these prior art inventions still have some problems in manufacturing them, for example, the laminating process of the porous material or mounting process of the guide are complicated, and the study of the formulation in the medication reservoir layer for conferring the adhesiveness is difficult.

The present invention has been developed to overcome the above-described problems, and an object of the present invention is to provide an electrode device used in iontophoresis treatment, wherein a medication-introducing electrode layer can reliably and closely contact with a medication reservoir layer by a simple manner, with which the medication reservoir layer can be stably held when a medication is introduced, and the medication reservoir layer can surely contact with the skin, to thereby make it possible to stably introduce the medication into a human body.

Means for Solving the Problems

The present invention provides an electrode device having the following features.

The electrode device of the present invention is used in iontophoresis treatment, wherein a medication reservoir layer containing ionized medication is placed in contact with a skin, and electric current is applied to the medication reservoir layer through a main-electrode layer to perform the iontophoresis treatment.

There are secured, on a substrate, the "main-electrode layer" and a "sub-electrode layer which is insulated from the main-electrode layer and which holds the medication reservoir layer on the substrate".

The medication reservoir layer is located on the substrate, so as to be in contact the main-electrode layer and the sub-electrode layer.

The medication reservoir layer is a gel containing halogen compound, and the sub-electrode layer comprises a metal having a lower ionization tendency than hydrogen. The medication reservoir layer and the sub-electrode layer are bonded to each other by applying an electric current to both the layers, to thereby hold the medication reservoir layer on the substrate while the medication reservoir layer is kept in contact with the main-electrode layer.

Here, the "main-electrode layer" means an electrode layer used for introducing the medication, while the "sub-electrode layer" means an electrode layer used for closely contact the main-electrode layer to the medication reservoir layer. That is, in the present invention, besides the main-electrode layer used for introduction of the medication, the sub-electrode layer is provided to contact the medication reservoir layer to the main-electrode layer.

The "medication reservoir layer" is needed to contain halogen compound. As the halogen compound, chlorine compound, bromine compound or iodine compound can be used, among which chlorine compound is preferably used. In addition, there is no particular limitation in selection of the gel forming the medication reservoir layer, insofar as the gel is hydrophilic. However, gel containing ion other than the ionized medication is not suitable for the medication reservoir layer for iontophoresis, because such the gel would lower transport number of the medication. As the preferable hydrophilic gel, there are exemplified polyvinyl alcohol, polyvinylpyrrolidone, a gellan gum and an agarose. Any of these gels may be used alone, or two or more thereof may be used as a mixture.

A metal species which can be employed as the "sub-electrode layer" is needed to have a lower ionization tendency than hydrogen. There can be exemplified antimony, bismuth, copper, mercury, silver, palladium, iridium, platinum and gold. Among those, silver is preferably used because of reactivity and practical usability. Above all, a thin silver film or a substrate film sheet formed by printing with paste containing silver particles is particularly preferable.

In the present invention, desirably, the "sub-electrode layer" and the "main-electrode layer" are located on a single sheet-like substrate. Even if the medication reservoir layer is bonded to the sub-electrode layer by applying an electric current, the main-electrode layer and the sub-electrode layer on separated substrates would make the contact between the main-electrode layer and the medication reservoir layer insufficient, possibly in turn the electric current would not flow when the introduction of the medication is intended. There is no particular limitation in selection of the sheet-like substrate. The sheet-like substrate can have recesses or protrusions or both, or the substrate can be flat.

In the present invention, for bonding the "medication reservoir layer" and the "sub-electrode layer" to each other, an electric current is needed to be applied between them. The sub-electrode layer side is connected to an anode, and the medication reservoir layer side is connected to a cathode, and an electric quantity of 1.0 mA·min./cm$^2$ or more is applied. When the electric quantity is smaller than that, the medication reservoir layer would not be bonded to the sub-electrode layer, or both layers are likely to peel off from each other with a small impact. To more firmly bond both the layers to each other, desirably, the electric quantity is 2.0 mA·min./cm$^2$ or more.

As described above, it is needed to apply an electric current in order to bond the "medication reservoir layer" to the "sub-electrode layer". To save an electric current and to prevent the characteristics change of the medication reservoir layer formed from the gel, the area of the sub-electrode layer is desirably made as small as possible. It is also possible to provide two or more sub-electrode layers, and the shape of the sub-electrode layer can be linear or dot-like as well as circular and rectangular. What is important is to locate the sub-electrode layer with appropriate size at proper position relative to the medication reservoir layer having a certain shape, so that the medication reservoir layer effectively contacts with the main-electrode layer.

When bonding the "medication reservoir layer" to the "sub-electrode layer", an auxiliary electrode is located on the back surface of the medication reservoir layer (i.e., the opposite surface to the sub-electrode layer), and an electric current is applied between the auxiliary electrode and the sub-electrode layer. At this time, a surface of the sub-electrode layer is halogenated, and thus the amount of the halogen in the medication reservoir layer is decreased, causing the characteristics of the gel to change. To minimize this characteristics change of the gel, the auxiliary electrode is desirably formed of a metal containing the same halogen, is coated with a halogenated metal, or is printed with paste containing particles of the metal containing the same halogen or the halogenated metal.

Further, when bonding the "medication reservoir layer" to the "sub-electrode layer", it is needed that an electric current applied to the "sub-electrode layer" should be prevented from passing through the "main-electrode layer". In case that this electric current passes through the main-electrode layer, the electric quantity used to bond the medication reservoir layer to the sub-electrode layer would be insufficient, resulting the incomplete bonding. Accordingly, the main-electrode layer and the sub-electrode layer are needed to be insulated from each other. This insulation can be done by an appropriate manner, for example desirably, a clearance is provided between both the layers, or an insulating layer is provided between both the layers. This insulating layer can be formed by printing.

Effect of the Invention

After intensive studies on the above-described problems of the prior arts, the present inventors found the following fact: that is, a hydrophilic gel containing a halogen compound is used as a medication reservoir layer; an electrode layer comprising a metal having a lower ionization tendency than hydrogen is made contact with the medication reservoir layer; and then an electric current is applied thereto for a given time; and these cause an attraction force to act between the medication reservoir layer and the electrode layer to thereby closely bond the both to each other.

However, it should be noted that if the electric current is directly applied to the "main-electrode layer" (which is originally intended for introducing the medication) for the purpose of contacting the main-electrode layer to the reservoir layer, the main-electrode layer would suffer an oxidation reaction due to the electric current being applied thereto. This would degrade the oxidation reactivity of the main-electrode layer for introducing the medication, and thus the main-electrode layer would not sufficiently work when introducing the medication. Then, it has been found that, for bonding the electrode layer to the medication reservoir layer, another "sub-electrode layer" may be newly provided, and that would solve the problems at once.

That is, firstly, an electric current is applied to the sub-electrode layer to thereby strongly bond the medication reservoir layer to the sub-electrode layer. This simultaneously causes the main-electrode layer and the medication reservoir layer to closely contact with each other. Thanks to this, during an electric current is applied to the main-electrode layer in later process, the medication reservoir layer and the main-electrode layer can be kept stably in contact, so that the medication can be reliably introduced into a human body.

In this way, only a simple process of applying an electric current between the sub-electrode layer and the medication reservoir layer can realize the close contact between the main-electrode layer and the medication reservoir layer. Thus, there is no need for laminating the porous material on the electrode layer, nor any guide to hold the gel. Further, it is not needed to confer adhesiveness to the gel, which means that there is no longer needed a study for a special formulation to confer the adhesiveness to the gel.

In the present invention, the medication reservoir layer is previously gelled. Therefore, the electrode device including the electrode layer is not needed to be subjected to freezing and thawing treatments, or to be exposed to an electron ray or UV, in order to form a gel. That is, it is possible to prevent dislocation of the electrode layer from the contact surface of the gel due to freezing and thawing. Further, it is possible to prevent characteristic change of the electrode layer due to the exposure to the electron ray or UV.

MODES FOR CARRYING OUT THE INVENTION

Hereinafter, the present invention will be described in more detail by way of Examples and exemplary tests, which however should not be construed as limiting the scope of the present invention in any way. In the following description, the unit % means percentage by weight, unless otherwise specified.

Example 1

The medication reservoir layer 5 to be used in iontophoresis treatment was prepared by the following procedure, and was then gelled.

| | |
|---|---|
| Completely hydrolyzed polyvinyl alcohol: | 15% |
| Sodium chloride: | 7.65% |
| Water: | 77.35% |
| Total: | 100% |

These components were heated, stirred and dissolved, and then spread to have a thickness of about 1 mm. This spread layer was frozen at −30° and was then thawed at a room temperature. The resultant gel was crosslinked to be shaped. After that, the shaped gel was punched out to obtain a disc with a diameter of 30 mm. This disc was used as the medication reservoir layer 5.

Figure 1:
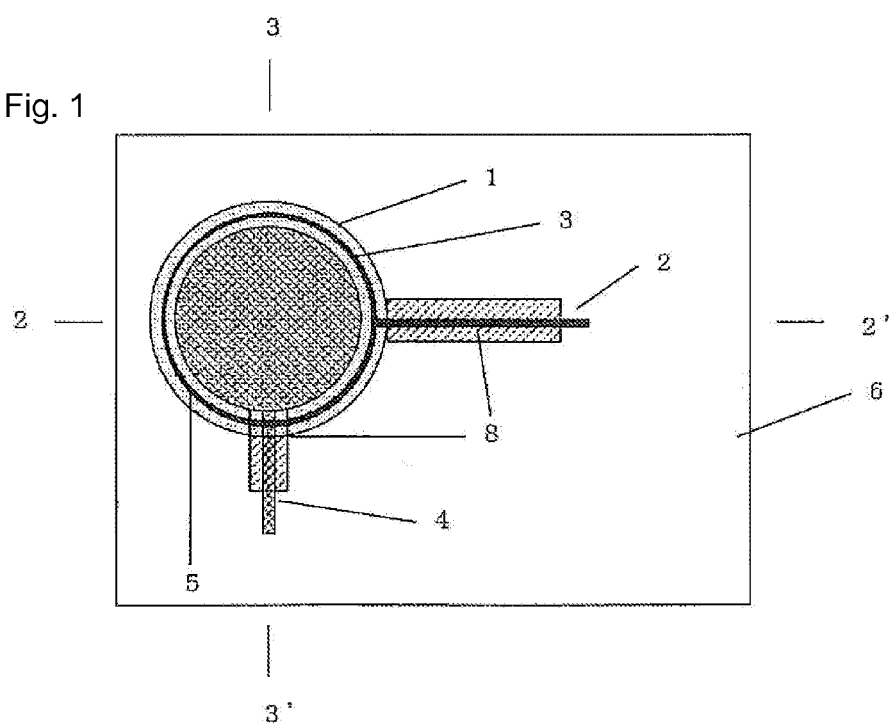
FIG. 1 shows the arrangement of the main-electrode layer, the sub-electrode layer, and the medication reservoir layer of the electrode device of Example 1.
Figure 2:
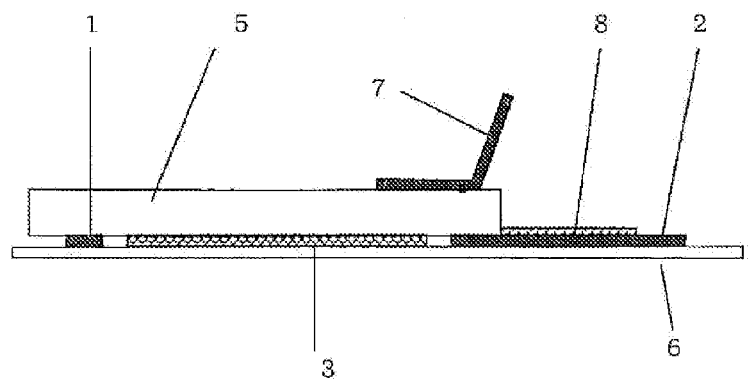
FIG. 2 shows a sectional view taken along the line 2-2' in FIG. 1.
Figure 3:
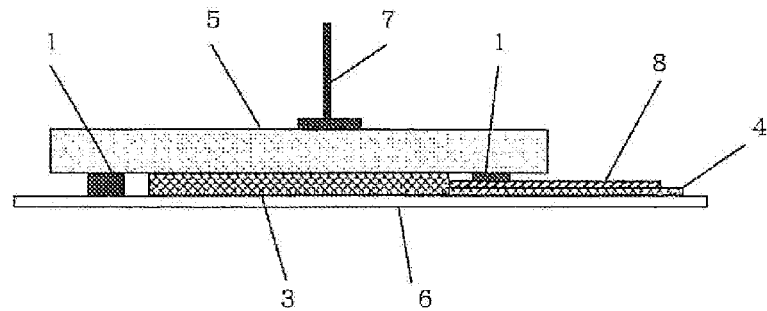
FIG. 3 shows a sectional view taken along the line 3-3' in FIG. 1.

FIG. 1 shows the arrangement of the respective members of the electrode device of Example 1. FIG. 2 shows a sectional view taken along the line 2-2' in FIG. 1; and FIG. 3 shows a sectional view taken along the line 3-3' in FIG. 1. In FIG. 1, the auxiliary electrode 7 shown in FIGS. 2 and 3 is omitted.

The substrate sheet 6 was a polyethylene terephthalate film with a thickness of 100 μm, a width of 100 mm and a length of 70 mm, on which the electrode device was assembled. Firstly, the main-electrode layer 3 and the sub-electrode layer 1 were formed on the substrate sheet 6. As described later, an electric current is applied to the sub-electrode layer 1 in manufacturing the electrode device, so that the shaped gel-like medication reservoir layer 5 is firmly secured to the substrate sheet 6. On the other hand, an electric current is applied to the main-electrode layer 3 in practical use of the electrode device, by which ions migrate into the skin. The main-electrode layer 3 was electrically insulated from the sub-electrode layer 1.

The main-electrode layer 3 was formed from paste containing silver particles and in the shape of a circle with a diameter of 27 mm on the substrate sheet 6, by screen printing. The main-electrode layer 3 is to be connected to an external power supply (not shown) via the lead 4, when the medication was introduced. The lead 4 was formed to have a width of 1 mm and a length of 15 mm, extending from a part of the main-electrode layer 3, by screen printing.

The intersecting area of the lead 4 and the sub-electrode layer 1 was coated with an insulating ink 8, thereby insulating the main-electrode layer 3 from the sub-electrode layer 1.

The sub-electrode layer 1 was formed from paste containing silver particles and in the shape of a ring with a width of 1 mm on the substrate sheet 6, by screen printing. The ring-shaped sub-electrode layer 1 was located around the main-electrode layer 3, with a space of 1 mm therebetween. The sub-electrode layer 1 is to be connected to the power supply 9 (see FIG. 5) via the lead 2. The lead 2 was formed to have a width of 1 mm and a length of 30 mm, extending from a part of the sub-electrode layer 1, by screen printing.

The lead 2 was coated with the insulating layer 8, except the connecting portion to the power supply 9.

Next, the disc-shaped medication reservoir layer 5 formed as above was placed on the main-electrode layer 3, so as to be evenly supported by the ring-shaped sub-electrode layer 1. Then, on the medication reservoir layer 5, the auxiliary electrode 7 formed from past containing silver chloride particles by screen printing was provided.

Figure 5:
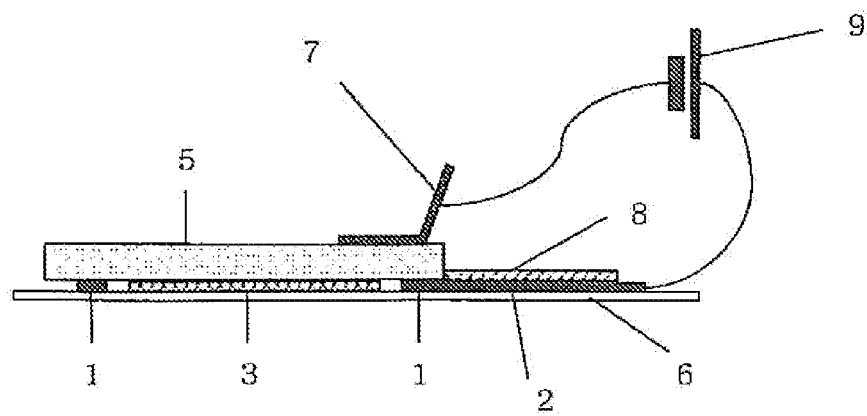
FIG. 5 shows the operation for attaching and bonding the sub-electrode layer to the medication reservoir layer by applying an electric current, in the electrode device shown in FIG. 1 (Example 1).

After that, as shown in FIG. 5, the negative terminal of the power supply was connected to the auxiliary electrode 7, while the positive terminal of the power supply was connected to the lead 2, which is in connection with the sub-electrode layer 1. Then, an electric current of 1.0 mA was applied for one minute, to thereby adhere and secure the sub-electrode layer 1 to the medication reservoir layer 5.

Example 2

The medication reservoir layer 5 to be used in iontophoresis treatment was prepared by the following procedure and was then gelled.

| | |
|---|---|
| Agarose: | 3% |
| Glycerin: | 10% |
| Sodium chloride: | 0.8% |
| Water: | 86.2% |
| Total: | 100% |

These components were heated, stirred and dissolved, and then spread to have a thickness of about 1 mm while it was still hot. This spread layer was cooled to a room temperature, and the resultant gel was crosslinked to be shaped. After that, the shaped gel was punched out to obtain a disc with a diameter of 30 mm. This disc was used as the medication reservoir layer 5

Figure 4:
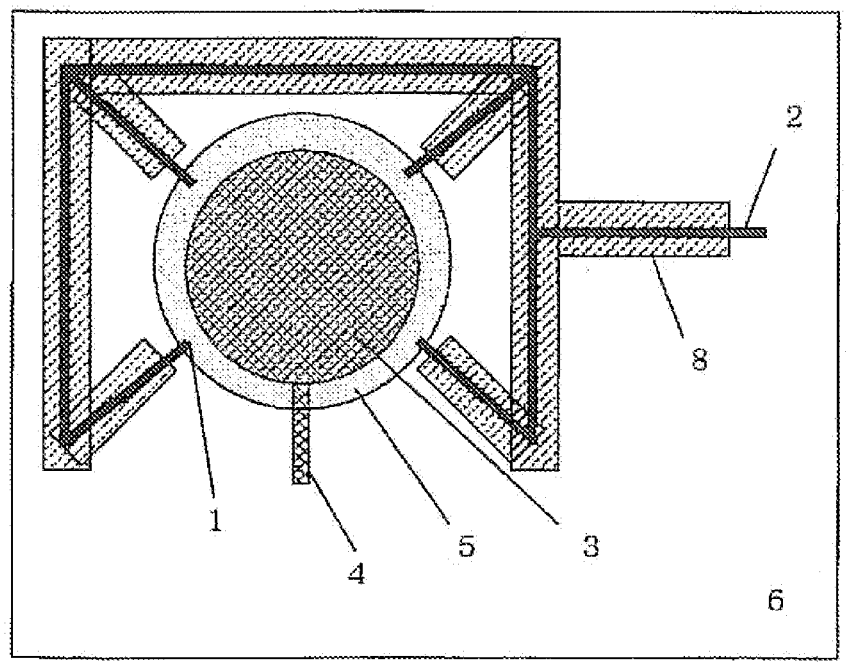
FIG. 4 shows the arrangement of the main-electrode layer, the sub-electrode layer, and the medication reservoir layer of the electrode device of Example 2.

FIG. 4 shows the arrangement of the respective members of the electrode device of Example 2. Like in Example 1, the substrate sheet 6 was a polyethylene terephthalate film with a thickness of 100 μm, a width of 100 mm and a length of 70 mm. The electrode device was assembled on this film.

The main-electrode layer 3 and the lead 4 were formed as one integrated member, which was cut out a silver foil with a thickness of 0.05 mm. This cut-out integrated member was adhered on the substrate sheet 6 with a double-sided tape. The portion for the main-electrode layer 3 was in the shape of a circle with a diameter of 27 mm. The portion for the lead 4 was in the shape of a rectangle with a width of 1 mm and a length of 15 mm, extending from a part of the main-electrode layer 3.

Likewise, the sub-electrode layer 1 was also prepared by cutting out a silver foil having a thickness of 0.05 mm, and then adhered on the substrate sheet 6 with a double-sided tape.

Four rectangular portions each having a width of 1 mm and a length of 15 mm were cut out of a silver foil. These were adhered so as to extend radially from four points of substantially equally spaced on a circle, which was 1 mm away from the outer periphery of the circular main-electrode layer 3. Then, the outer ends of the radially arranged four rectangular portions were connected to one another through a silver foil strip having a width of 1 mm, from where the connection lead 2 was branched to the power supply 9 (see FIG. 5).

Except for the areas of 2 mm length of the sub-electrode layer 1 on the side of the main-electrode layer 3, and for the connecting portion of the lead 2 to the power supply 9, the entire circuit connecting the sub-electrode layer 1 to the power supply 9 was covered by Cellotape® to provide the insulating layer 8.

Next, the disc-shaped medication reservoir layer 5 formed as above was placed on the main-electrode layer 3, so as to be evenly supported by the four non-insulated end portions of the sub-electrode layer 1. Then, on the medication reservoir layer 5, the auxiliary electrode 7 formed from past containing silver chloride particles by screen printing was provided.

After that, as shown in FIG. 5, the negative terminal of the power supply 9 was connected to the auxiliary electrode 7, while the positive terminal of the power supply 9 was connected to the lead 2 of the sub-electrode layer 1. Then, an electric current of 1.0 mA was applied for one minute, to thereby adhere and bond the sub-electrode layer 1 to the medication reservoir layer 5.

Comparative Example 1

Except that the "sub-electrode layer" was not bonded to the "medication reservoir layer" by application of an electric current, a "medication reservoir layer" was prepared in the same manner as in Example 1, and a similar electrode device was obtained.

Comparative Example 2

Except that the "sub-electrode layer" was not bonded to the "medication reservoir layer" by application of an electric current, a "medication reservoir layer" was prepared in the same manner as in Example 2, and a similar electrode device was obtained.

Exemplary Test 1

Bonding Force Test 1

Each of the electrode devices of Examples 1 and 2 and Comparative Examples 1 and 2 was gently turned upside down. As a result, in Comparative Example 2, the medication reservoir layer 5 was separated from the electrode layers, peeling and falling off the sheet substrate 6.

On the other hand, in each of Examples 1 and 2 and Comparative Example 1, the medication reservoir layer 5 was still bonded to the sheet substrate 6. An end of each bonded medication reservoir layer 5 was pinched up with a tweezers to evaluate the bonding degree. As a result, the medication reservoir layer 5 of Comparative Example 1 was easily peeled off the sheet substrate 6, while the medication reservoir layers 5 of Examples 1 and 2 showed a stronger bonding force enough to bring up the sheet substrates together.

Exemplary Test 2

Bonding Force Test 2

For each of Examples 1 and 2 and Comparative Example 1, two electrode devices were prepared. One of the two electrode devices was used as a donor patch for iontophoresis, and the other was used as a reference patch, both of the electrode devices being adhered to the back of a rat. Then, an electric current of 0.7 mA was applied through the main-electrode layers of the both patches, and the fluctuation in voltage was observed.

As a result, no fluctuation in voltage was observed in Examples 1 and 2, and stable electric current was observed. On the other hand, in Comparative Example 1, the medication reservoir layers got dislocated from the main-electrode layers when the patches were adhered to the back of the rat, so that an electric current flowed with a voltage slightly higher than those in Examples 1 and 2. Further, in Comparative Example 1, the gel remained on the skin of the rat when the patches were peeled off after completion of the electric current application.

Further, it was found that, in the region where the medication reservoir layer got dislocated from the main-electrode layer, an electrode portion which became not in contact with the gel due to such the dislocation did not work. This result suggested that, in Comparative Example 1, the electrode layer and the medication reservoir layer were not sufficiently contacted, and thus possibly a stable electric current could not be obtained when the medication was introduced. In case that the medication reservoir layer got dislocated from the main-electrode layer, the main-electrode layer could not make its performance sufficiently.

Generally, when dermal administration of a biologically active substance is conducted by iontophoresis, it is designed that a predetermined amount of electric current may flow into a predetermined area. The reason for such designing may be that uneven electric current would possibly induce damages on the skin. Further, in case that the medication reservoir layer peeled off the electrode layer, or the medication reservoir layer got dislocated from the electrode layer, the main-electrode layer would be likely naked. Then, the electric current would flow directly into the skin without passing through the medication reservoir layer. As a result, undesired effect may be brought, for example, a degradation of efficiency for introducing medication. Therefore, the electrode devices of Comparative Examples 1 and 2 are considered insufficient for use in iontophoresis.

On the other hand, it was found that the electrode devices of Examples 1 and 2 can provide stable electric currents, because the medication reservoir layer and the electrode layer were contacted firmly.

Exemplary Test 3

Bonding Force Test 3

Figure 6:
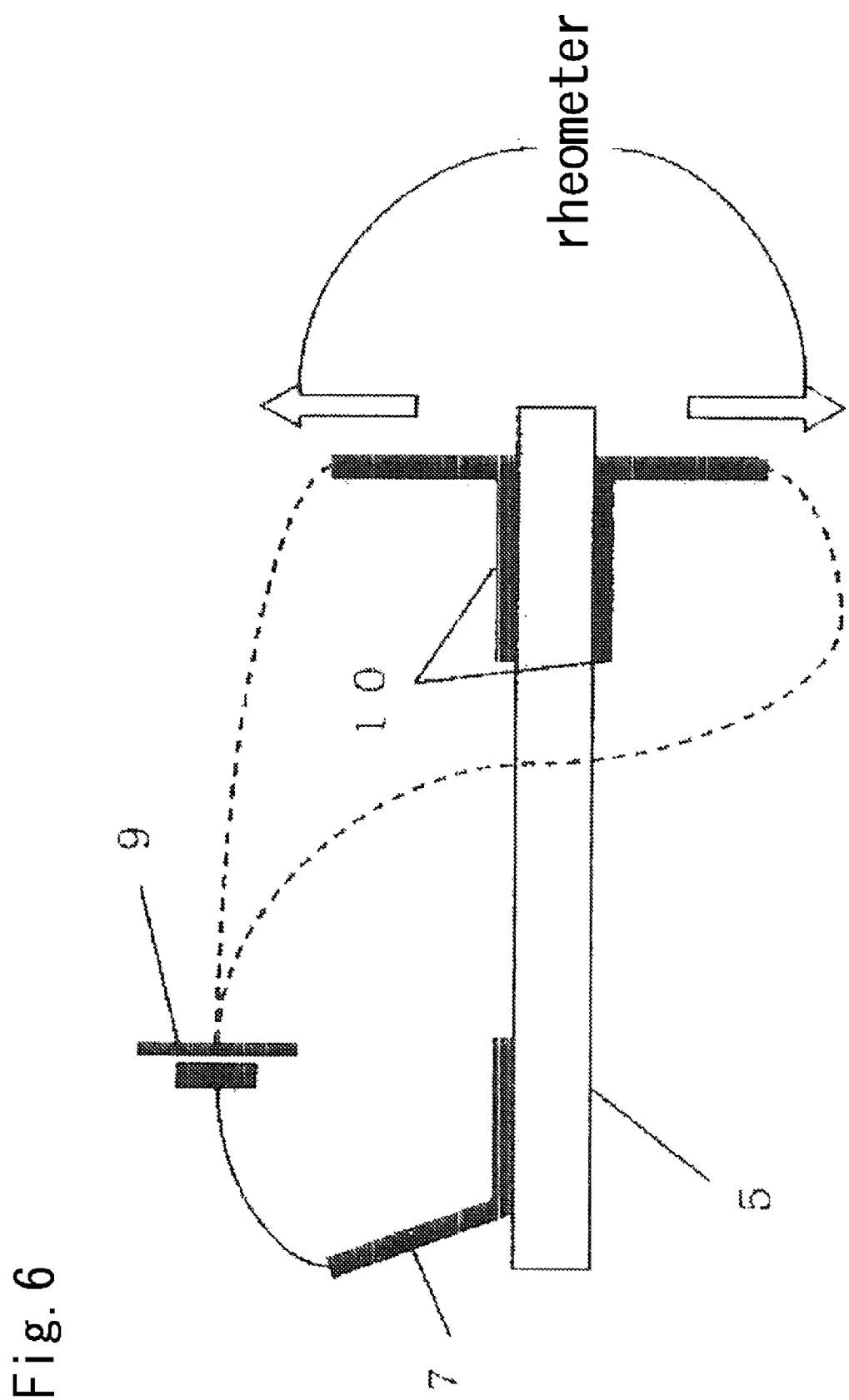
FIG. 6 shows the schematic diagram of the exemplary test 3.

To find a relationship between the electric quantity and the bonding strength, a peel test using a rheometer was conducted. FIG. 6 schematically shows the peel test. Firstly, a medication reservoir layer 5 was prepared, having the same components as those used in Example 1. Besides, two rectangular sheets of silver foils 10 (0.05 mm thickness×10 mm width×20 mm height) were separately prepared. Each of the rectangular silver foils was folded a right angle at its point of 10 mm height. Each one side of the two foils was made contact with the medication reservoir layer 5, so that the medication reservoir layer 5 was sandwiched between the two silver foils 10.

Further, a silver foil 7 coated with a silver chloride film was made contact with the medication reservoir layer 5, so that the silver foil 7 did not contact with the two silver foils 10 (if the silver foil 7 contacts with the silver foils 10, a possible short circuit prevent bonding of the gel 5 and the silver foils 10). The positive terminal of the power supply was connected to one of the silver foils 10, and the negative terminal was connected to the silver foil 7 coated with the silver chloride film, and then an electric current was applied for one minute. Next, the positive terminal was switched to be connected to the other silver foil 10, and then the same amount of an electric current was applied for one minute. Thus, the two silver foils 10 were adhered and secured to the both surfaces of the gel 5. The Peel test was conducted on the two silver foils 10, using a rheometer (Model CR-500DX manufactured by SUN SCIENTIFIC CO., LTD.) to measure the peel strength of the silver foils.

Figure 7:
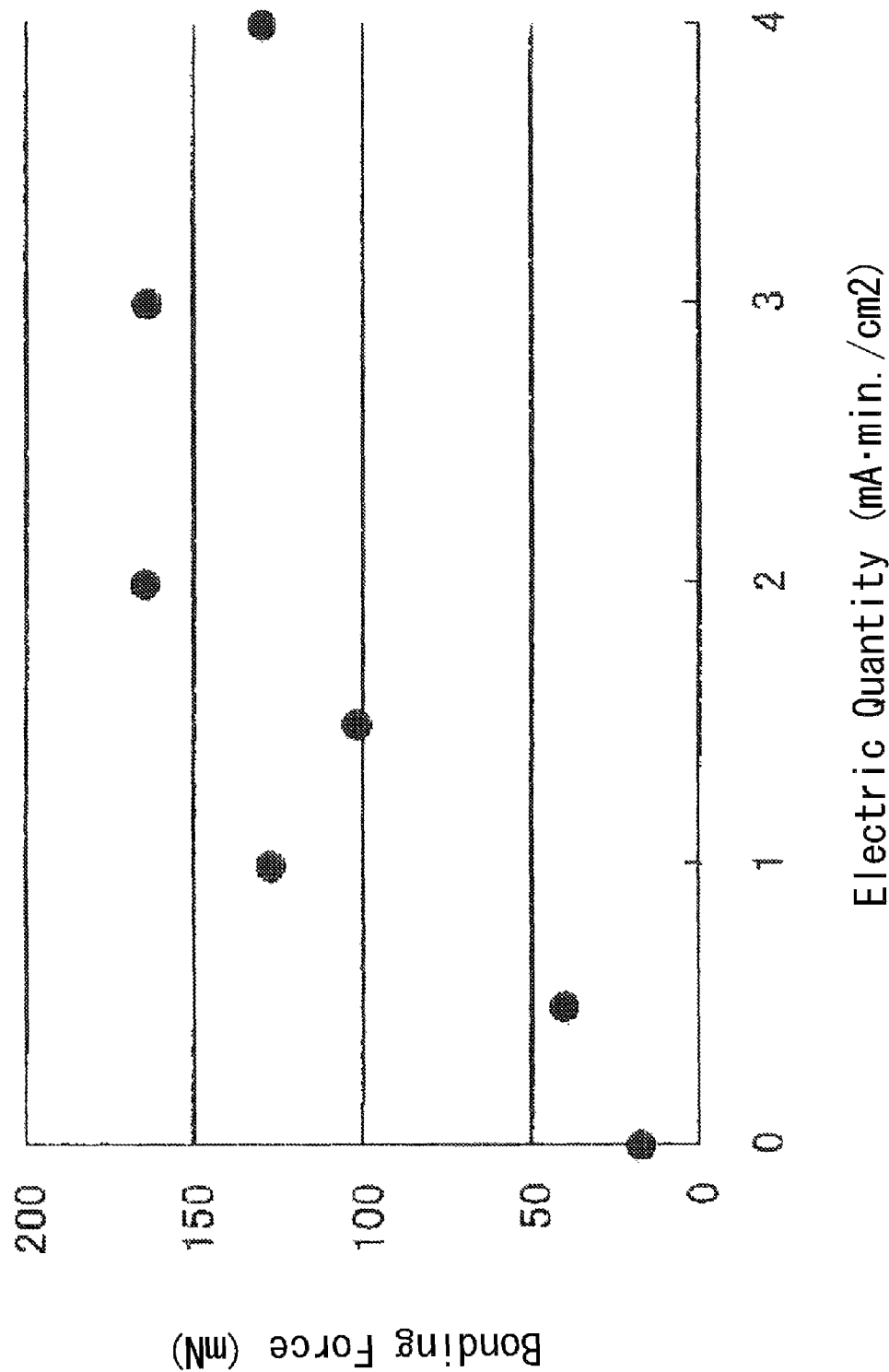
FIG. 7 shows a graph illustrating a relationship between an electric quantity applied to the sub-electrode layer and the bonding strength.

For some samples wherein silver foils 10 are bonded to a medication reservoir layer 5 with various electric quantity, the peel strengths were measured in the same way. The results are shown in FIG. 7.

According to this graph, it is found that the more the electric current flows, the higher the bonding force becomes between the medication reservoir layer 5 (the gel) and the electrode layer, and that a peel strength from 100 to 200 mN is obtained at 1 mA·min./cm$^2$ or more.

Regarding a gel equivalent to what in Example 1 used in this test, the gel was torn when the applied tensile strength exceeded about 100 mN, and thus a bonding strength could not be measured above that strength (this fact indicates that the bonded portion had a bonding strength of at least 100 mN or more).

Any of the bonding force tests 1 to 3 shows the effectiveness of the bonding strength between "the medication reservoir layer" and "the sub-electrode layer", which was obtained according to the present invention, utilizing the electric current.

DESCRIPTION OF REFERENCE NUMERALS

1: sub-electrode layer
2: lead for the sub-electrode layer
3: main-electrode layer
4: lead for the main-electrode layer
5: medication reservoir layer
6: substrate sheet
7: auxiliary electrode for bonding use
8: insulating layer
9: external power supply
10: silver foil

The invention claimed is:

1. An electrode device used in iontophoresis treatment, comprising a substrate, a medication reservoir layer, a main-electrode layer and a sub-electrode layer, wherein the medication reservoir layer containing ionized medication is placed in contact with a skin, and an electric current is applied to the medication reservoir layer through the main-electrode layer to perform the iontophoresis treatment, wherein:

the main-electrode layer and the sub-electrode layer are secured on the substrate, wherein the sub-electrode layer is insulated from the main-electrode layer and holds the medication reservoir layer on the substrate;

the medication reservoir layer is located on the substrate, so as to be in contact with the main-electrode layer and the sub-electrode layer;

the medication reservoir layer is a gel containing halogen compound, and the sub-electrode layer comprises a metal having a lower ionization tendency than hydrogen; and the medication reservoir layer and the sub-electrode layer are bonded to each other, wherein the bonding of the medication reservoir layer and the sub-electrode layer is effected by applying an electric current to the medication reservoir layer and the sub-electrode layer, to thereby hold the medication reservoir layer on the substrate while the medication reservoir layer is in contact with the main-electrode layer.

2. The electrode device of claim 1, wherein the halogen compound is chlorine compound.

3. The electrode device of claim 2, wherein an electric quantity used for bonding the medication reservoir layer to the sub-electrode layer is 1.0 mA·min./cm$^2$ or more.

4. The electrode device of claim 2, wherein an electric quantity used for bonding the medication reservoir layer to the sub-electrode layer is 2.0 mA·min./cm$^2$ or more.

5. The electrode device of claim 1, wherein an electric quantity used for bonding the medication reservoir layer to the sub-electrode layer is 1.0 mA·min./cm$^2$ or more.

6. The electrode device of claim 1, wherein an electric quantity used for bonding the medication reservoir layer to the sub-electrode layer is 2.0 mA·min./cm$^2$ or more.

* * * * *